(12) United States Patent
Kamat et al.

(10) Patent No.: US 9,643,976 B2
(45) Date of Patent: May 9, 2017

(54) SOLVATES OF DARUNAVIR (71) Applicants: Anand Gopalkrishna Kamat, Hyderabad (IN); Naga Trinadhachari Ganala, Hyderabad (IN); Venkata Balaji Boddu, Hyderabad (IN); Joseph Prabahar Koilpillai, Hyderabad (IN); Sivakumaran Meenaakshisunderam, Hyderabad (IN)

(72) Inventors: Anand Gopalkrishna Kamat, Hyderabad (IN); Naga Trinadhachari Ganala, Hyderabad (IN); Venkata Balaji Boddu, Hyderabad (IN); Joseph Prabahar Koilpillai, Hyderabad (IN); Sivakumaran Meenaakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 13/261,929

(22) PCT Filed: Jan. 11, 2013

(86) PCT No.: PCT/IB2013/000037
§ 371 (c)(1),
(2) Date: Jul. 11, 2014

(87) PCT Pub. No.: WO2013/108105
PCT Pub. Date: Jul. 25, 2013

(65) Prior Publication Data
US 2015/0141382 A1  May 21, 2015

(30) Foreign Application Priority Data

Jan. 18, 2012 (IN) .............................. 199/CHE/2012
Jun. 11, 2012 (IN) ........................... 2314/CHE/2012

(51) Int. Cl.
*C07D 493/04* (2006.01)

(52) U.S. Cl.
CPC ................................. *C07D 493/04* (2013.01)

(58) Field of Classification Search
None
See application file for complete search history.

(56) References Cited

U.S. PATENT DOCUMENTS

2005/0250845 A1* 11/2005 Vermeersch ......... C07D 493/04
514/456

OTHER PUBLICATIONS

Strickley (Pharmaceutical Research, vol. 21, No. 2, Feb. 2004, pp. 201-230).*

* cited by examiner

*Primary Examiner* — Kortney L Klinkel
*Assistant Examiner* — William Lee
(74) *Attorney, Agent, or Firm* — Jay R Akhave; Patent Science LLC.

(57) ABSTRACT

The present invention relates to novel solvates of Darunavir of Formula I.

I

13 Claims, 8 Drawing Sheets

SOLVATES OF DARUNAVIR

FIELD OF THE INVENTION

The present invention relates to novel solvates of Darunavir of Formula I.

I

BACKGROUND OF THE INVENTION

Darunavir is a potent HIV protease inhibitor, which is chemically known as [(1S,2R)-3-[[(4-Aminophenyl)sulfonyl](2-methylpropyl)amino]-2-hydroxy-1-(phenylmethyl)propyl]carbamic acid, (3R,3aS,6aR)-hexahydrofuro[2,3-b]furan-3-yl ester, represented by Formula I.

Darunavir is a new generation of non-peptide protease inhibitor (PI). It is exceeding potent and has shown impressive broad-spectrum activity against highly cross-resistant HIV mutants. Darunavir is being marketed under the brand name Prezista® as an oral tablet and oral suspension in the form of monoethanolate solvate.

Prezista® must be co-administered with Ritonavir to exert its therapeutic effect. Failure to correctly co-administer Prezista® with Ritonavir will result in plasma levels of Darunavir that will be insufficient to achieve the desired antiviral effect and will alter some drug interactions.

Darunavir is generically disclosed in U.S. Pat. No. 5,843,946, specifically disclosed in U.S. Pat. No. 6,248,775. However, in these patents, there is no specific example for preparing Darunavir.

U.S. Pat. No. 6,248,775 discloses a process for preparing 2R-hydroxy-3-[[4-aminophenyl) sulfonyl](2-methylpropyl)amino]-1S-(phenylmethyl)propylamine, which is referred as Diamino alcohol a compound of Formula II,

II a key intermediate in the preparation of Darunavir.
The process is as shown below:

anhydrous methylene chloride
triethylamine
4-nitrobenzenesulfonyl chloride

Ethylacetate
10% Pd-C
Hydrogen

II

This process involves the use of benzyloxycarbonyl (Cbz) protection, which needs to be deprotected by catalytic hydrogenation using palladium on carbon catalyst and hence the process is not industrially and commercially cost effective.

Bioorganic Medicinal Chemistry Letters 8, 1998, 687-690, discloses a process to prepare Darunavir as well as Diamino alcohol a compound of Formula II, which is as shown below:

isopropylalcohol i) $H_2N$-⟨⟩-$SO_2Cl$
Py
ii) $H_2$, 10% Pd-C

II

This process involves the use of highly hazardous azide intermediate and hence not suitable for commercial production.

U.S. Pat. No. 7,772,411 B2 discloses a process to prepare Diamino alcohol a compound of Formula II, which is as shown below:

isobutylamine after the completion of epoxide condensation with isobutylamine. The unwanted isobutylamine reacts with p-nitrobenzenesulfonyl chloride to give the N-isobutyl 4-nitrobenzenesulfonamide impurity of Formula XI.

XI

Further, this N-isobutyl 4-nitrobenzenesulfonamide impurity of Formula XI, participate in the next reactions to give corresponding impurities.

3. Sulfonamide reaction is carried out at higher temperature i.e., 82-88° C., wherein the product undergoes degradation and observed that the reaction mass becomes very thick, which is very difficult to stir/mix.

The present inventors has repeated the above process and found the following disadvantages:

1. Diamino alcohol preparation was carried out in one pot and the purity of obtained product was found to low.

2. Unwanted reactions observed during the formation of nitro compound (A), which is due to the existence of 4. The isolation of Diamino alcohol is tedious, wherein it involves pH adjustment, water content adjustment and concentration.

In view of the above and to overcome the prior-art problems the present inventors have now developed an improved process for the preparation of Diamino alcohol having high purity and yield, which is further converted to Darunavir or its pharmaceutically acceptable salts, solvates thereof, having high yield and purity.

U.S. Pat. No. 7,700,645 discloses several pseudopolymorphs of Darunavir, including the ethanolate, hydrate, methanolate, acetonate, dichloromethanoate, ethyl acetate, 1-methoxy-2-propanolate, anisolate, tetrahydrofuranate, isopropanolate and mesylate solvates; US 2011/0313035 discloses Darunavir $C_{5-8}$ alcohol solvate, wherein $C_{5-8}$ alcohol solvate is selected from 2-methyl-2-butanol and n-pentanol; US 2012/0035142 discloses Darunavir dimethylsulfoxide solvate, Tetrahydrofuran solvate.

New polymorphic forms and solvates of a pharmaceutically useful compound or salts thereof can also provide an opportunity to improve the performance characteristics of a pharmaceutical product and new solvates of Darunavir that may have advantageous physico-chemical and biokinetic properties such as suitable solubility in neutral, acidic or alkaline water medium, solubility in technologically important organic solvents, water/lipid partition coefficient, electrochargeability, thermal stability, water and oxygen inertness, hygroscopicity, crystal shape, particle size and surface, dissolution profile, compatibility with excipients and combined active ingredients or special properties for final dosage form design.

Journal of Organic Chemistry 2004, 69, 7822-7829 discloses a process for preparing amorphous Darunavir, by purifying Darunavir by column chromatography.

European Journal of Pharmaceutical Sciences 2009, 38, 489-497 discloses processes for the preparation of amorphous Darunavir.

by melting Darunavir hydrate or ethanolate on a Kofler hot bar and cooling by dissolving Darunavir ethanolate in MDC and spray drying The prior-art processes involve the use of chromatographic and spray drying techniques. Hence, there is a need in the art to develop an improved process for the preparation of amorphous Darunavir.

The present inventors have found that Darunavir ethanolate is hygroscopic and converts to Darunavir hydrate at moderate or high relative humidity at 25° C. Further, the isolation of Darunavir ethanolate involves special precautions during isolation, drying and powder processing, which is onerous during the large scale manufacturing of Darunavir ethanolate.

In view of the above, the present inventors have now developed novel solvates of Darunavir, which are stable solvates and does not require laborious isolation. Further, the present inventors developed an improved process for the preparation of amorphous Darunavir from Darunavir or its solvates thereof.

OBJECTIVE OF THE INVENTION

The main objective of the present invention is to provide novel solvates of Darunavir, which are stable.

Yet another objective of the present invention is to provide pharmaceutical compositions comprising Darunavir solvate and use thereof in treating retroviral infections and, in particular, HIV infection Yet another objective of the present invention is to provide an improved process for to the preparation of Darunavir or its pharmaceutically acceptable salts, solvates thereof, which is simple, industrially applicable and economically viable.

Yet another objective of the present invention is to provide a process for preparing amorphous Darunavir, which is simple and industrially applicable.

SUMMARY OF THE INVENTION

The present invention relates to novel solvates of Darunavir, wherein the solvate is glycol or glycol ethers. Preferred glycol are ethylene glycol, propylene glycol (1,2-propanediol), trimethylene glycol (1,3-propanediol) and glycol ether is 2-methoxyethanol.

In another aspect of the present invention is to provide a process for the preparation of novel solvates of Darunavir, which comprises:
   a) treating Darunavir with glycol or glycol ethers, optionally in presence of a solvent; and
   b) isolating Darunavir solvate.
wherein glycol is selected from group comprising of ethylene glycol, propylene glycol, trimethylene glycol; glycol ether is selected from group comprising 2-methoxyethanol.

In another aspect of the present invention is to provide an improved process for the preparation of Darunavir in amorphous form, which comprises:
   a) treating Darunavir or its solvates thereof in water and/or water miscible solvent; and
   b) isolating amorphous Darunavir.

In another aspect of the present invention is to provide an improved process for the preparation of Darunavir of Formula I, or its pharmaceutically acceptable salts, solvates thereof, which comprises,
   a) reacting epoxide compound of Formula V,

V wherein P represents a protecting group
with isobutylamine in presence or absence of a solvent to give a compound of Formula VII;

VII wherein P represents a protecting group
   b) optionally, isolating compound of Formula VII;
   c) reacting compound of Formula VII with p-nitrobenzenesulfonyl halide or its acid addition salt to give a compound of Formula VIII or acid addition salt thereof,

VIII wherein P is same as defined above which is free of impurity compound of Formula XI;

d) deprotecting the compound of Formula VIII or acid addition salt thereof, to give a compound of Formula IX or acid addition salt thereof;

IX e) reducing the compound of Formula IX or acid addition salt thereof to give Diamino alcohol of Formula II or acid addition salt thereof;

II f) condensing compound of Formula II with 1-[[[(3R,3aS, 6aR)-hexahydrofuro[2,3-b]furan-3-yloxy]carbonyl] oxy]-2,5-pyrrolidine-dione of Formula X,

X in a solvent to give Darunavir of Formula I; and g) optionally, converting Darunavir of Formula I in to its pharmaceutically acceptable salt, solvate thereof.

DETAILED DESCRIPTION OF THE INVENTION

Figure 1:
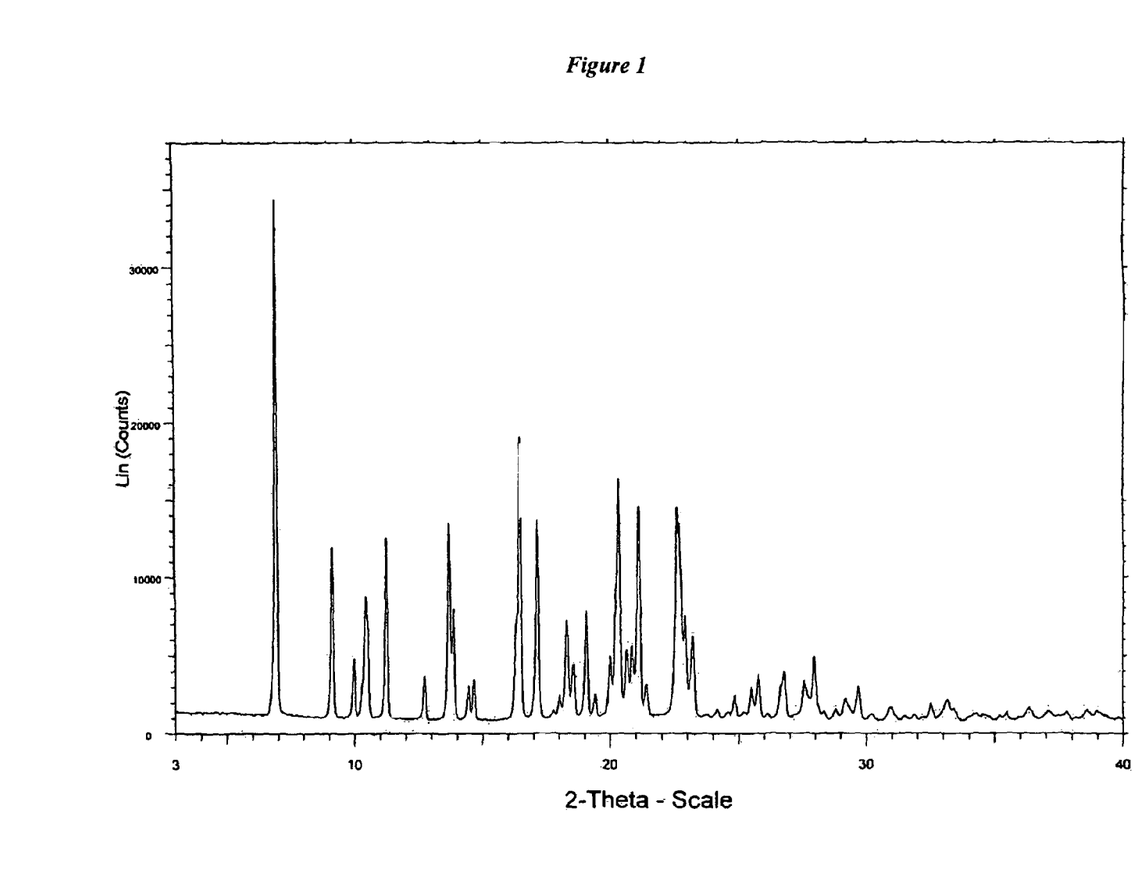
FIG. 1—Powder X-ray diffraction pattern of Darunavir trimethylene glycol solvate.
Figure 2:
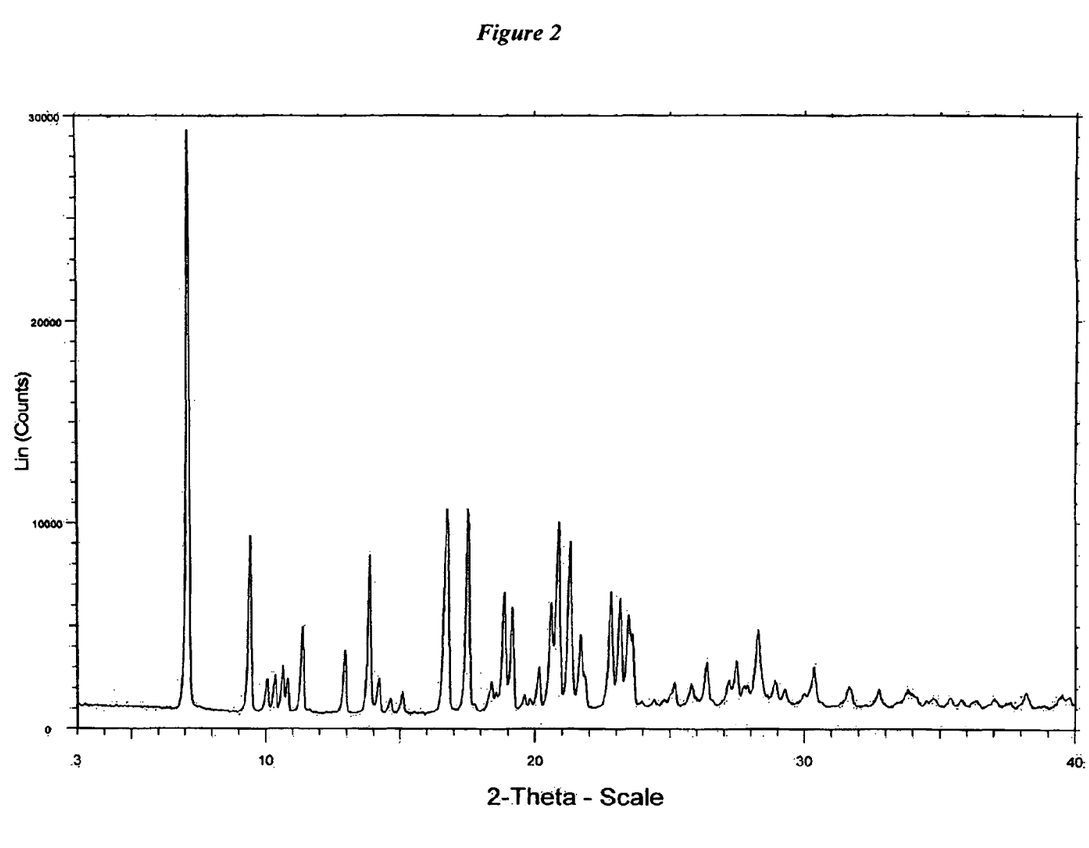
FIG. 2—Powder X-ray diffraction pattern of Darunavir ethylene glycol solvate.
Figure 3:
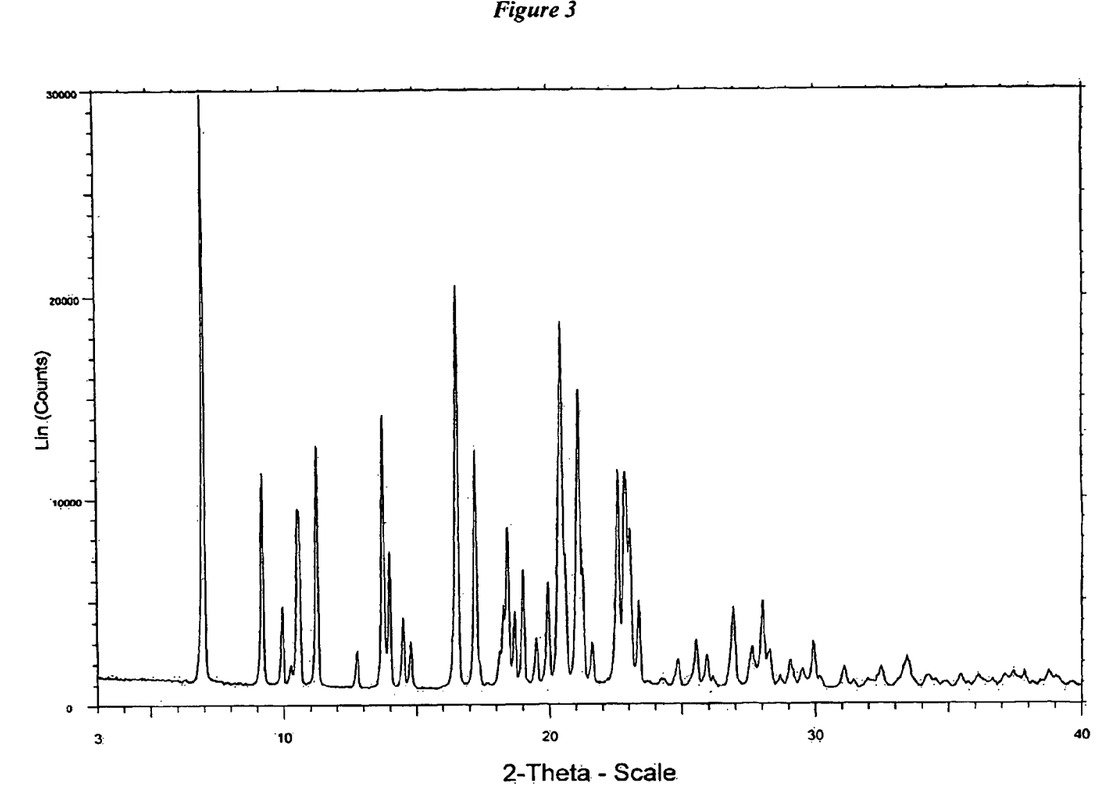
FIG. 3—Powder X-ray diffraction pattern of Darunavir propylene glycol solvate.
Figure 4:
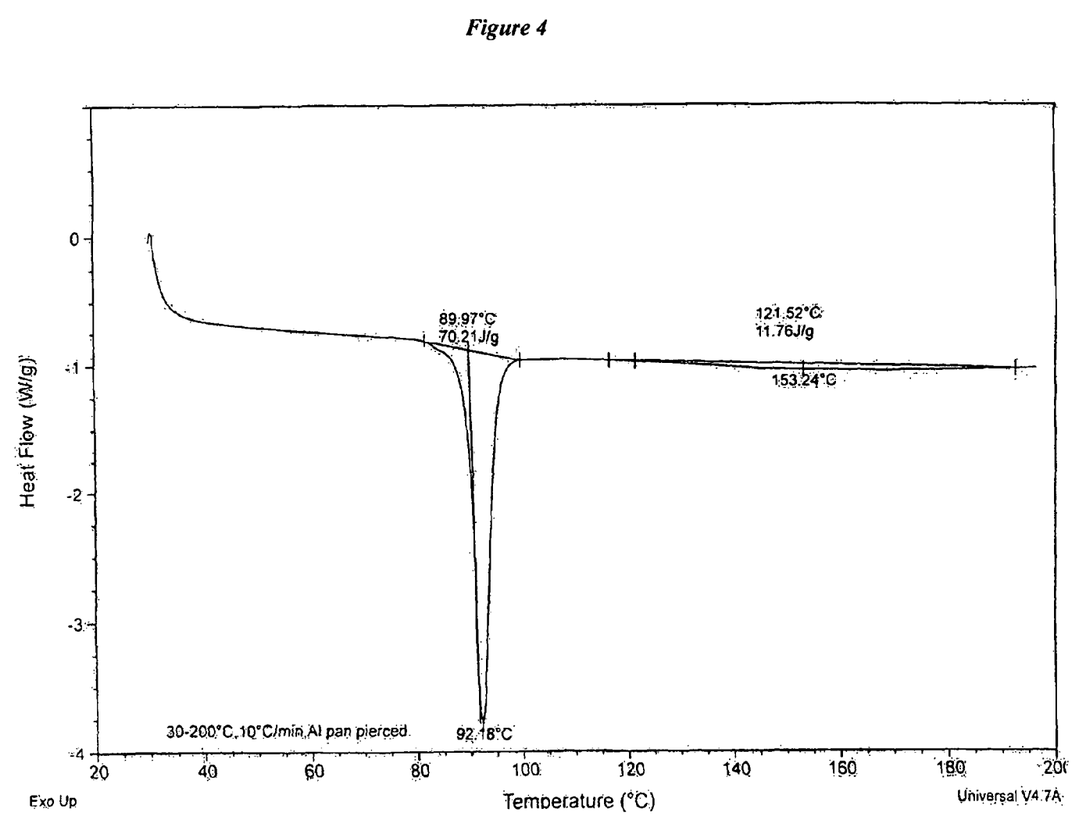
FIG. 4—DSC of Darunavir propylene glycol solvate.
Figure 5:
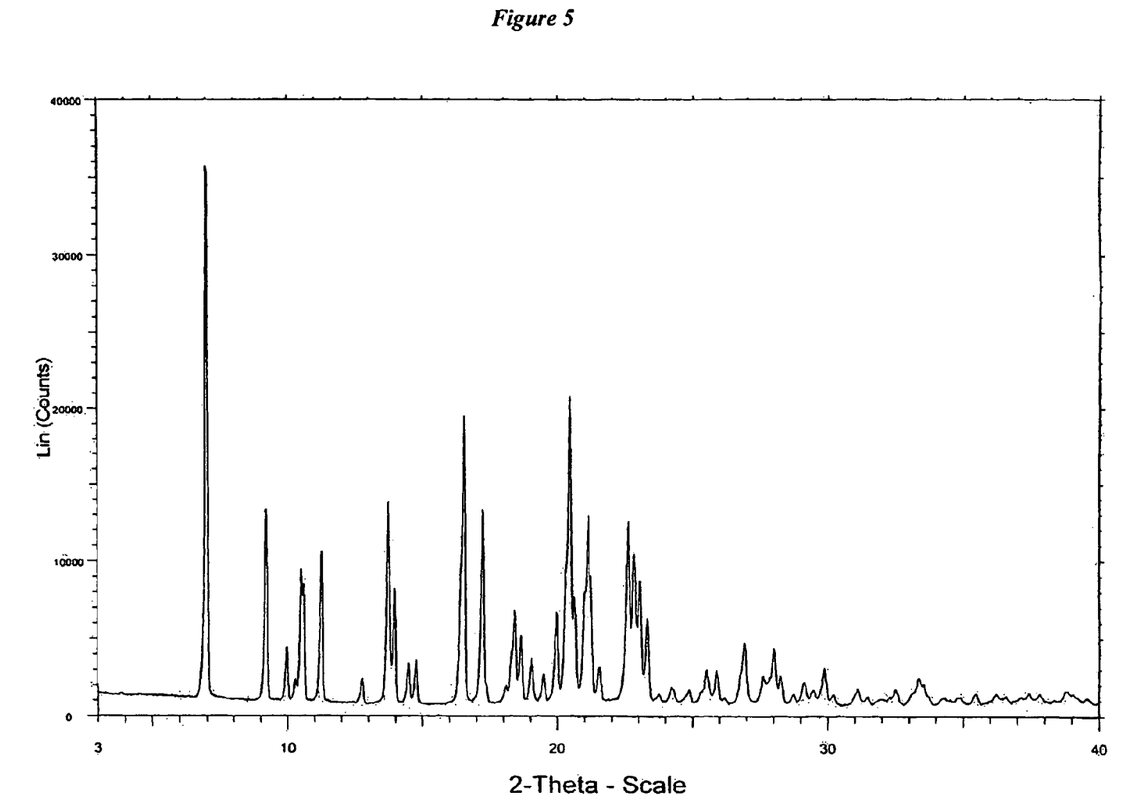
FIG. 5—Powder X-ray diffraction pattern of Darunavir methoxyethanol solvate.
Figure 6:
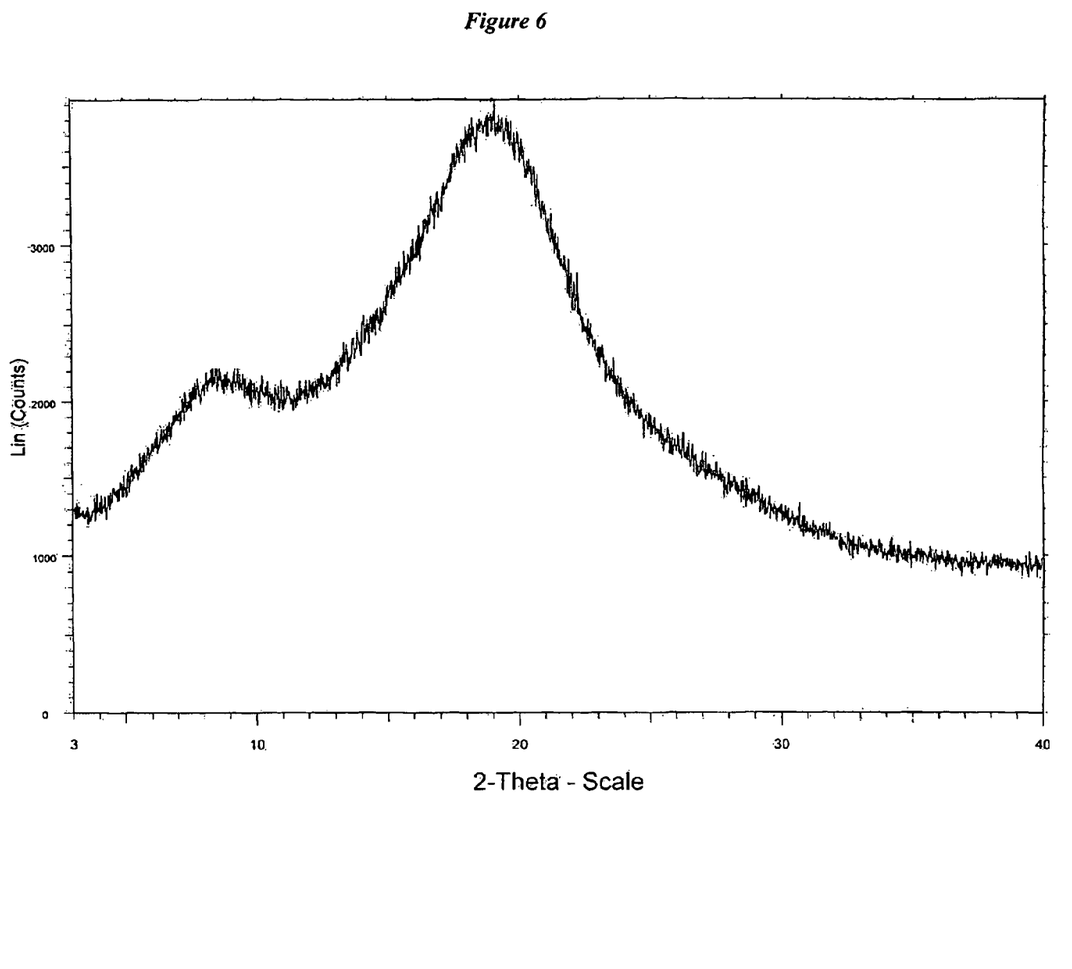
FIG. 6—Powder X-ray diffraction pattern of amorphous Darunavir.
Figure 7:
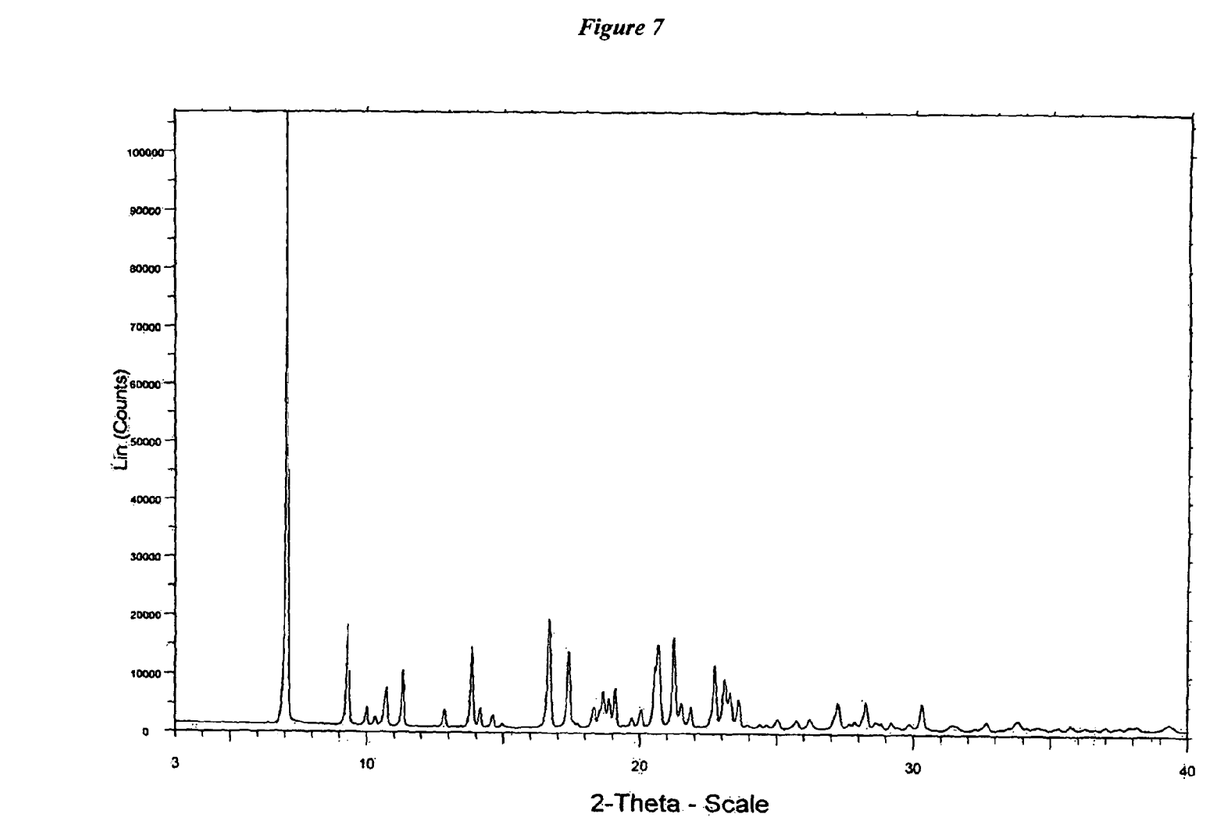
FIG. 7—Powder X-ray diffraction pattern of Darunavir ethanolate solvate.
Figure 8:
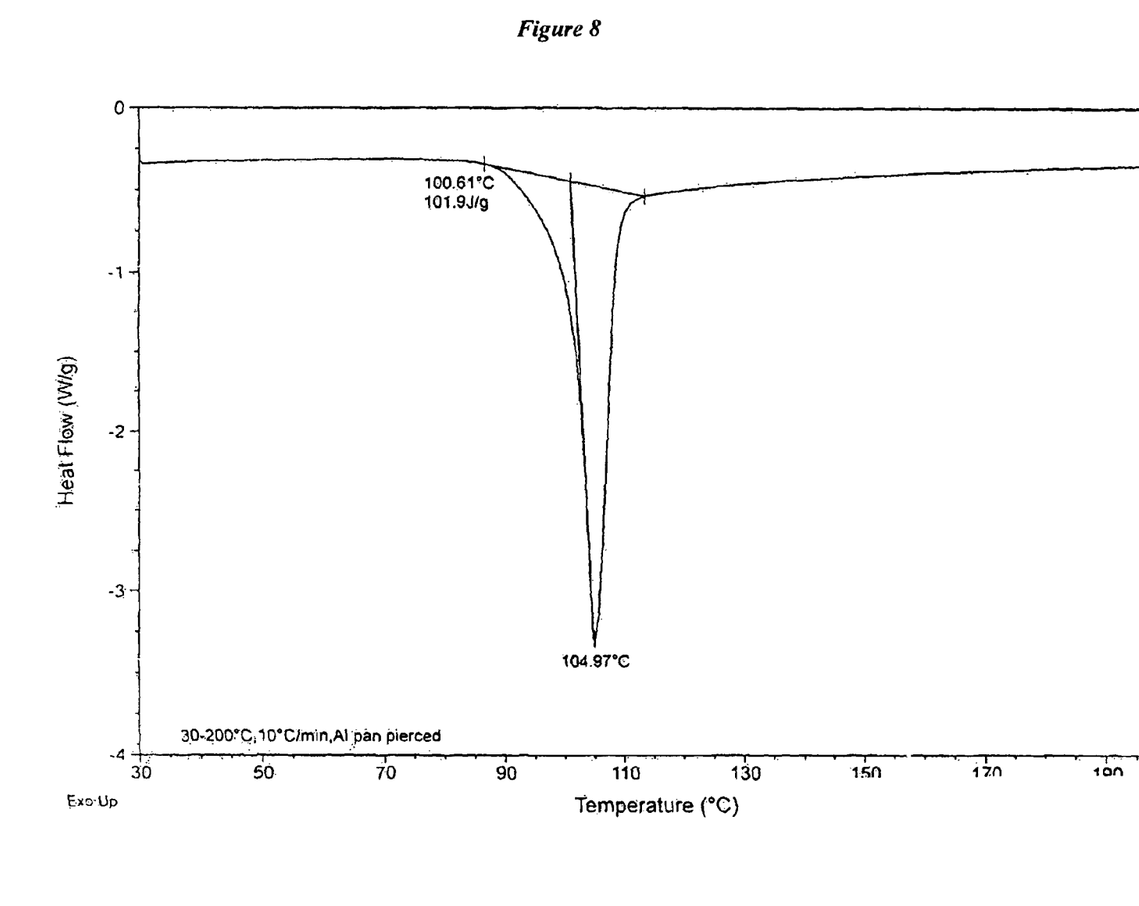
FIG. 8—DSC of Darunavir ethanolate solvate.

The present invention relates to novel solvates of Darunavir, wherein the solvate is glycol or glycol ethers. The preferred glycol's are selected from the group comprising ethylene glycol, propylene glycol (1,2-propanediol), trimethylene glycol (1,3-propanediol) and glycol ether is selected from the group comprising 2-methoxyethanol.

Another aspect of the present invention is to provide a process for the preparation of Darunavir glycol solvate, by treating Darunavir with glycol, optionally in presence of a solvent, selected from methyl tert-butylether or diisopropylether and isolating Darunavir glycol solvate, wherein glycol is selected from the group comprising ethylene glycol, propylene glycol, trimethylene glycol.

Another aspect of the present invention is to provide a process for the preparation of Darunavir 2-methoxyethanol solvate, by treating Darunavir with 2-methoxyethanol, optionally in presence of a solvent, selected from methyl tert-butylether or diisopropylether and isolating Darunavir 2-methoxyethanol solvate.

In another aspect of the present invention the ratio of Darunavir to glycol or glycol ether is about 1:1.

The present inventors have compared the hygroscopicity of Darunavir propylene glycolate of the present invention with Darunavir ethanolate under the conditions of hygroscopic testing (at 25° C.±2° C. and 80% RH±2° C. for 24 h). The results obtained are as tabulated:

| Product | Initial (Solvent content) | Final (Solvent content) |
| --- | --- | --- |
| Darunavir ethanolate | 6.75% | 0.67% |
| Darunavir propylene glycolate | 11.51% | 10.37% |

In both the cases the solvent is replaced correspondingly with water. However, the content of solvent replaced in Darunavir propylene glycolate is very low when compared with solvent replaced in Darunavir ethanolate. Hence, Darunavir propylene glycolate is less hygroscopic and stable when compared to Darunavir ethanolate.

The present inventors have also studied the stability of Darunavir propylene glycolate at 40° C. and 75% RH for 3 months and found that the product complies with the initial results and found to be stable.

In another aspect of the present invention the isolation of Darunavir glycol or glycol ether solvates is carried out by way of cooling, anti solvent technique, evaporation of solvent, filtration techniques etc.

Another aspect of the present invention is to provide a process for preparing Darunavir in amorphous form, by treating Darunavir or its solvate thereof in water and/or water miscible solvent selected from methanol, ethanol, isopropanol, acetone, at a temperature ranging from 5-40° C., preferably at 25-30° C. and isolating amorphous Darunavir, wherein solvate is selected from ethanolate, ethylene glycol solvate, propylene glycol solvate, trimethylene glycol solvate, 2-methoxyethanol solvate.

The isolated amorphous Darunavir is dried at a temperature 55-60° C. using different methods, such as under atmospheric pressure, under reduced pressure, by circulation drying, flow drying or fluidized bed drying till water content is less than 1.2%.

In another aspect of the present invention is to provide a process for preparing Darunavir of Formula I, or its pharmaceutically acceptable salts, solvates thereof, reacting epoxide compound of Formula V with isobutylamine in presence or absence of a solvent, selected from alcohols, such as methanol, ethanol, isopropanol; ethers such as tetrahydrofuran, dioxane; hydrocarbons such as toluene, xylene, cyclohexane, hexane; halogenated hydrocarbons such as methylene chloride, ethylene chloride, chloroform; N,N-dimethylformamide, N,N-dimethylacetamide, dimethylsulfoxide or mixtures thereof at a temperature ranging from 35-140° C., preferably at 70-75° C. to give a isobutylaminocarbamate of Formula VII.

After the completion of the reaction the obtained isobutylaminocarbamate of Formula VII in a solvent is washed with water and adjusted the pH to ~8 for removing the excess or left over isobutylamine in the reaction mass.

| As per US '411 Impurity of Formula XI (by HPLC) | Present invention Impurity of Formula XI (by HPLC) |
|---|---|
| ~27% | Not detected |

The isobutylaminocarbamate of Formula VII is optionally isolated or in situ condensed with p-nitrobenzenesulfonyl halide, in a solvent selected from methylene chloride, chloroform, toluene, xylene, ethylenechloride in presence of an acid scavenger selected from non-nucleophilic inorganic or organic bases, such as triethylamine, diisoproylethylamine, tributyl amine, N,N-dimethyl aniline, pyridine, DBN, DBU at a temperature ranging from −10 to 100° C., preferably at 15-30° C. to give compound of Formula VIII or acid addition salt thereof.

The compound of Formula VIII is deprotected using a suitable deprotecting agent and a solvent depending upon the protecting group to give compound of Formula IX or acid addition salt thereof, preferably monohydrochloride salt having a purity >99.8% by HPLC. Acetyl group, which is deprotected with a base, selected from ammonium, sodium hydroxide, potassium hydroxide, lithium hydroxide; 9-Fluorenylmethyloxycarbonyl (FMOC), which is deprotected using piperidine; tert-Butyloxycarbonyl group, which is deprotected using an acid, selected from hydrochloric acid, trifluoroacetic acid. The solvent is selected from alcohols such as methanol, ethanol, isopropanol, ten-butyl alcohol, ethers such as tetrahydrofuran; dioxane, esters such as ethyl acetate, methyl acetate, hydrocarbons such as toluene; xylene, water, or mixture thereof.

Examples of reagents and methods for deprotecting amines from amino protecting groups can additionally be found in Protecting Groups in Organic Synthesis by Theodora W. Greene, New York, John Wiley and Sons. Inc. 1981.

The compound of Formula IX or acid addition salt thereof is reduced to give Diamino alcohol or acid addition salt thereof of Formula II, preferably monohydrochloride salt having a purity >99.8% by HPLC, using a reducing agent selected from borane complexes, metals such as iron, tin, zinc; transition metals such as palladium-carbon, platinum oxide, Raney nickel in presence of hydrogen or hydrogen source selected from ammonium formate, sodium dihydrogen phosphate, hydrazine in a solvent selected from alcohols, such as methanol, ethanol, isopropanol, tert-butyl alcohol; esters such as ethyl acetate, methyl acetate; toluene; xylene; tetrahydrofuran; dioxane or mixture thereof at a temperature ranging from 5-50° C., preferably at 25-30° C.

The Diamino alcohol or acid addition salt thereof of Formula II is condensed with 1-[[[(3R,3aS,6aR)-hexahydrofuro[2,3-b]furan-3-yloxy]carbonyl]oxy]-2,5-pyrrolidine of Formula X in a solvent selected from methylene chloride, chloroform, methanol, acetonitrile, tetrahydrofuran at a temperature ranging from −40 to 50° C., preferably at −25 to −15° C. to give Darunavir of Formula I.

In another aspect of the present invention the acid addition salt of compound of Formula VIII; compound of Formula IX and compound of Formula II (Diamino alcohol) is selected from hydrochloride, hydrobromide, sulfate, preferably as hydrochloride salt.

In another aspect of the present invention is to provide pharmaceutical composition comprising Darunavir glycol or glycol ether solvate and one or more pharmaceutically acceptable excipients.

In another aspect of the present invention is to provide pharmaceutical composition comprising Darunavir propylene glycol solvate and one or more pharmaceutically acceptable excipients.

In another aspect of the present invention is to provide an oral pharmaceutical composition in a solid oral dosage form, such as a tablet, which is optionally film coated.

In another aspect, the present invention is to provide an oral pharmaceutical composition comprising Darunavir propylene glycol solvate and one or more pharmaceutically acceptable excipients, wherein the composition is substantially free of co-processed spray-dried mixture of microcrystalline cellulose and colloidal silicon dioxide.

The oral pharmaceutical composition of Darunavir propylene glycol solvate may be prepared by direct compression, wet granulation or roll compaction. Specifically, the oral pharmaceutical composition of Darunavir solvate is prepared by direct compression.

The oral pharmaceutical composition may contain one or more additional excipients such as diluents, binders, disintegrants and lubricants. Exemplary diluents include lactose, sucrose, glucose, mannitol, sorbitol, calcium carbonate, microcrystalline cellulose such as Prosolv®, magnesium stearate and mixtures thereof. Specifically, the diluent is Prosolv®. Exemplary binders are selected from L-hydroxy propyl cellulose, polyvinyl pyrrolidine, hydroxylpropyl methyl cellulose, hydroxylethyl cellulose and pre-gelatinized starch. Exemplary disintegrants are selected from croscarmellose sodium, crospovidone, sodium starch glycolate and low substituted hydroxylpropyl cellulose. In a specific embodiment, the disintegrant is low substituted hydroxylpropyl cellulose and crospovidone. Exemplary lubricants are selected from sodium stearyl fumarate, magnesium stearate, zinc stearate, calcium stearate, stearic acid, talc, glyceryl behenate and colloidal silicon dioxide. A specific lubricant is selected from magnesium stearate, zinc stearate, calcium stearate and colloidal silicon dioxide.

In another aspect of the present invention also provide a method of preventing the development of drug resistance of HIV in an HIV-infected mammal by administration of a drug resistance-inhibiting effective amount of Darunavir propylene glycol solvate.

The following examples illustrate the nature of the invention and are provided for illustrative purposes only and should not be construed to limit the scope of the invention.

Example 1

Preparation of (1S,2R)-3-[[4-(aminophenyl)-sulfonyl](2-methylpropyl)amino]-2-hydroxy-1-(phenylmethyl)propyl]amine hydrochloride (Diamino alcohol Monohydrochloride)

a) Preparation of (1S,2R)-[3-(2-methylpropylamino)]-2-hydroxy-1-(phenylmethyl)-carbamic acid, tert-butyl ester (2S)-[(1'S)-(tert-Butoxycarbonyl)amino-2'-phenylethyl]oxirane (250 g) and isobutylamine (750 ml) were heated at 70-75° C. for 3 h. Thereafter, the reaction mass was cooled to 55-60° C. and concentrated under reduced pressure at below 60° C. to remove isobutylamine. The residue is dissolved in methylene chloride (3000 ml) and diluted with DM water (1000 ml). The pH of the reaction mass was adjusted to ~8 with aqueous hydrochloride and separated the organic layer. This organic layer containing [(1S,2R)-[3-(2-methylpropylamino)]-2-hydroxy-1-(phenylmethyl)carbamic acid, tert-butyl ester was taken as such for the next step.

b) Preparation of [(1S,2R)-3-[[(4-Nitrophenylsulfonyl)(2-methylpropyl)]amino]-2-hydroxy-1-(phenyl methyl)propyl]carbamic acid, tert-butyl ester Triethylamine (105.60 g) was added to the methylene chloride solution of step (a), at 20-22° C. Thereafter, to the resulting reaction mixture a solution of 4-nitrobenzenesulfonyl chloride (221.10 g) in methylene chloride (750 ml) was added at 15-30° C. over a period of 1 h and the mass was stirred at 25-30° C. for 1 h. The reaction mixture was washed sequentially with DM water (500 ml), aqueous sodium bicarbonate solution (2×750 ml) and water (500 ml) at 25-30° C. This solution containing [(1S,2R)-3-[[(4-nitrophenylsulfonyl)(2-methylpropyl)]amino]-2-hydroxy-1-(phenyl methyl)propyl]carbamic acid, tert-butyl ester was taken as such for the next step.

c) Preparation of (1S,2R)-3-[[4-(Nitrophenyl)sulfonyl](2-methylpropylamino)]-2-hydroxy-1-(phenyl methyl)propyl]-amine as its hydrochloride salt. (Amino nitro alcohol hydrochloride)

Methylene chloride solution of step (b) was concentrated at 30-45° C. under reduced pressure. To the concentrated mass, ethanol (2375 ml) and hydrochloric acid (~35% w/w, 170 ml) was added and heated at 75-80° C. for 1 h. Thereafter the reaction mixture was cooled to 5-10° C. and stirred at this temperature for 1 h. The product obtained was filtered, washed with ethanol (440 ml) and dried at 45-55° C. under reduced pressure to obtain amino nitro alcohol hydrochloride.

Yield: 330 g

Chromatographic Purity (by HPLC): 99.92% d) Preparation of (1S,2R)-3-[[4-(Aminophenyl)sulfonyl](2-methylpropyl)amino]-2-hydroxy-1-(phenylmethyl)propyl]amine Hydrochloride (Diamino alcohol monohydrochloride)

Amino nitro alcohol hydrochloride (260 g) obtained as per step (c) was suspended in methanol (2600 ml) at 0.25-30° C. and hydrogenated in the presence of Raney nickel catalyst (13 g) under 4-6 Kg/cm$^2$ pressure at 25-30° C. for 10 h. After completion of the reaction, the catalyst was filtered and the filtrate was concentrated at 40-55° C. under reduced pressure to remove methanol. The residue was stirred in toluene (1040 ml) at 40-50° C. for 20 min, thereafter cooled to 25-30° C. and stirred at this temperature for 1 h. The product obtained was filtered, washed with toluene (120 ml) and dried at 45-50° C. under reduced pressure to obtain diamino alcohol monohydrochloride.

Yield: 221 g

Chromatographic Purity (by HPLC): 99.97%

Example 2

Preparation of (1S,2R)-[3-(2-Methylpropyl-amino)]-2-hydroxy-1-(phenylmethyl) carbamic acid tert-butyl ester (2S)-[(1'S)-(tert-Butoxycarbonyl)amino-2'-phenylethyl]oxirane (200 g) and isobutylamine (600 ml) were heated to 70-75° C. for 3 h. Thereafter, the reaction mass was concentrated under reduced pressure to remove isobutylamine. The obtained residue was dissolved in a mixture of toluene (500 ml) and diisopropyl ether (1600 ml) at 45-50° C., cooled to 10-15° C. and stirred at 10-15° C. for about 1 h. The product was filtered, washed with pre-cooled diisopropyl ether (400 ml, 10-15° C.) and dried at 45-50° C. under reduced pressure to yield title compound as white solid.

Yield: 231 g

Chromatographic Purity (by HPLC): 99.41%

Example 3

Preparation of [(1S,2R)-3-[[(4-Nitrophenylsulfonyl)(2-methylpropyl)]amino]-2-hydroxy-1-(phenyl methyl)propyl]carbamic acid tert-butyl ester (1S,2R)-[3-(2-Methylpropyl-amino)]-2-hydroxy-1-(phenylmethyl) carbamic acid tert-butyl ester (170 g) was dissolved in methylene chloride (2040 ml) and added triethylamine (56.20 g) at 15-20° C. Thereafter, a solution of 4-nitrobenzenesulfonyl chloride (117.70 g) in methylene chloride (510 ml) was added to the above solution at 15-30° C. and stirred at 25-30° C. for 1 h. After completion of the reaction the reaction mixture was washed sequentially with DM water (340 ml), aqueous sodium bicarbonate solution (2×425 ml) and DM water (340 ml) at 25-30° C. The organic layer was concentrated under reduced pressure at 30-45° C. Toluene (1530 ml) was added to the residue, stirred at 50-55° C. for 30 min, thereafter cooled to 25-30° C. and stirred at this temperature for 1 h. The obtained product was filtered, washed with toluene (170 ml) and dried at 50-55° C. under reduced pressure to obtain title compound.

Yield: 260 g

Chromatographic Purity (by HPLC): 99.95%

Example 4

Preparation of (1S,2R)-3-[[4-(Nitrophenyl)-sulfonyl](2-methylpropylamino)]-2-hydroxy-1-(phenylmethyl)propyl]amine hydrochloride. (Amino nitro alcohol hydrochloride)

[(1S,2R)-3-[[(4-Nitrophenylsulfonyl)(2-methylpropyl)]amino]-2-hydroxy-1-(phenyl methyl)propyl]carbamic acid tert-butyl ester (220 g) was dissolved in ethanol (2200 ml) and hydrochloric acid (~35% w/w, 77 ml) was added at 75-80° C. The reaction mixture was stirred at 75-80° C. for 1 h. Thereafter the reaction mass was cooled to 5-10° C. and stirred for 1 h. The product obtained was filtered, washed with ethanol (440 ml) and dried at 45-55° C. under reduced pressure to obtain Amino nitro alcohol hydrochloride.

Yield: 173 g
Chromatographic purity (by HPLC): 99.89%
Chloride content: 7.7% w/w
$^1$H NMR (300 MHz, DMSO-$d_6$): δ 8.38 (d, 2H), 8.05-8.09 (m, 5H), 7.29-7.36 (m, 5H), 5.62 (d, 1H), 3.96 (m, 1H), 3.33-3.43 (m, 2H), 2.96-3.08 (m, 3H), 2.83-2.89 (m, 2H), 1.88-1.91 (m, 1H), 0.82 (d, 3H), 0.75 (d, 3H).

Example 5

Preparation of (1S,2R)-3-[[4-(Aminophenyl)-sulfonyl](2-methylpropyl)amino]-2-hydroxy-1-(phenylmethyl)propyl]amine Hydrochloride (Diamino alcohol monohydrochloride)

Amino nitro alcohol hydrochloride (120 g) was suspended in methanol (1200 ml) at 25-30° C. and hydrogenated in the presence of Raney nickel catalyst (36 g) under 5-6 Kg/cm$^2$ pressure at 25-30° C. for 2 h. After completion of the reaction, the catalyst was filtered and the filtrate was concentrated at 40-55° C. under reduced pressure to remove methanol. The residue was stirred in toluene (480 ml) at 50-55° C. for 20 min, thereafter cooled to 25-30° C. and stirred at this temperature for 1 h. The product obtained was filtered, washed with toluene (120 ml) and dried at 45-50° C. under reduced pressure to obtain Diamino alcohol monohydrochloride.

Yield: 103 g
Chromatographic purity (by HPLC): 99.90%
Chloride content: 8.2% w/w
$^1$H NMR (500 MHz, DMSO-$d_6$): δ 7.88 (brs, 3H), 7.27-7.39 (m, 7H), 6.62 (d, 2H), 6.04 (s, 2H), 5.55 (d, 1H), 4.01 (m, 1H), 3.46 (m, 1H), 3.34 (m, 1H), 3.0-3.1 (m, 1H), 2.72-2.89 (m, 3H), 2.59-2.72 (m, 1H), 1.88-1.91 (m, 1H), 0.83 (d, 3H), 0.75 (d, 3H).

Example 6

Preparation of Darunavir

To the mixture of Diamino alcohol monohydrochloride (5 g), methylene chloride (50 ml), DM water (15 ml), 10% w/w aqueous sodium hydroxide solution (5 ml) was added to adjust the pH to 10 at 20-30° C. The organic layer was separated and washed with DM water (10 ml). Methylene chloride extract was dried over anhydrous sodium sulphate and 1 [[[(3R,3aS,6aR)-hexahydrofuro[2,3-b]furan-3-yloxy]carbonyl]oxy]-2,5-pyrrolidine-dione (3.17 g) was added and cooled to 5-10° C. Thereafter, triethylamine (1.18 g) was added and the temperature of reaction mass was raised to 25-30° C. and stirred at this temperature for 3 h. The reaction mass was washed with 7% w/w aqueous sodium bicarbonate solution (20 ml), followed by DM water (2×15 ml) and then concentrated under reduced pressure at 30-40° C. to obtain Darunavir as viscous oily mass.

Yield: 8 g (Viscous oily mass)

Example 7

Preparation of Amorphous Darunavir

Darunavir (3 g) was dissolved in methanol (4 ml) at 45-50° C. and diluted with DM water (20 ml). Thereafter, the mass was concentrated at 40-50° C. under reduced pressure to a volume of ~18 ml, which was cooled to 25-30° C. and stirred at this temperature for 15 h. The obtained solid was filtered, washed with DM water and dried at 55-60° C. under reduced pressure to obtain amorphous Darunavir.

Yield: 2.2 g
Water content (by Karl-Fisher): 0.71%

Example 8

Preparation of Darunavir Propylene Glycol Solvate

Triethylamine (70.90 g) was added to methylene chloride (750 ml) solution of Diamino alcohol monohydrochloride (150 g) and 1-[[[(3R,3aS,6aR)-hexahydro furo[2,3-b]furan-3-yloxy]carbonyl]oxy]-2,5-pyrrolidinedione (90.30 g) at −25° C. to −15° C. and stirred for 2 h. The reaction mass was treated with monomethylamine (solution in methanol, ~20% w/w, 6.0 g) for 30 min. The reaction mass was sequentially washed with ~7% w/w aqueous sodium bicarbonate solution (300 ml), ~2% w/w aqueous hydrochloric acid (2×300 ml), ~7% w/w aqueous sodium bicarbonate solution (300 ml) and water (300 ml) at 5-25° C. Thereafter, methylene chloride solution was treated with carbon (7.50 g) and concentrated under reduced pressure at 30-40° C. The residue was dissolved, in a mixture of propylene glycol (300 ml) and methyl tert-butyl ether (300 ml) and stirred at 25-30° C. for 12 h. The resulting slurry was cooled to 2-5° C. and stirred at this temperature for 2 h. The product was filtered, washed with methyl tert-butyl ether (150 ml) and dried at 50-55° C. under reduced pressure to obtain Darunavir propylene glycolate.

Yield: 172 g
Chromatographic purity (by HPLC): 99.84%
DSC: Single endotherm peak at 94.93° C.
Propylene glycol content: 11.48% w/w

Example 9

Preparation of Darunavir Ethanolate

Triethylamine (56.70 g) was added to the mixture of diamino alcohol monohydro chloride (120 g), 1-[[[(3R,3aS,6aR)-hexahydrofuro[2,3-b]furan-3-yloxy]carbonyl]oxy]-2,5-pyrrolidinedione (73.80 g) and methylene chloride (600 ml) at −25° C. to −15° C. and stirred for 2 h. The reaction mass was treated with monomethyl amine (solution in methanol, ~20% w/w, 4.70 g) for 30 min. The reaction mass was sequentially washed with ~7% w/w aqueous sodium bicarbonate solution (240 ml), ~2% w/w aqueous hydrochloric acid (2×240 ml), ~7% w/w aqueous sodium bicarbonate solution (240 ml) and water (240 ml) at 5-25° C. Thereafter, methylene chloride solution was treated with carbon (6.0 g) and concentrated under reduced pressure at 30-40° C. The residue was stirred with ethanol (600 ml) at 50-55° C. for 30 min. The resulting slurry was cooled to 25-30° C. and stirred at this temperature for 1 h. The product was filtered, washed with ethanol (120 ml) and dried at 40-50° C. under reduced pressure to obtain Darunavir ethanolate.

Yield: 133 g
Chromatographic purity (by HPLC): 99.86%
DSC: Single endotherm peak at 104.97° C.
Ethanol content: 7.40% w/w

Example 10

Preparation of Darunavir Ethylene Glycol Solvate

Ethylene glycol (30 ml) was added to Darunavir (1.0 g) at 30-40° C. and stirred at 45-50° C. under reduced pressure for 20 minutes. The resulting solution was cooled to 25-30° C. and stirred at this temperature for 5 h. The separated product was filtered, washed with ethylene glycol (6 ml) and dried at 45-50° C. under reduced pressure to obtain Darunavir ethylene glycol solvate.

Yield: 6.2 g

Example 11

Preparation of Darunavir Propylene Glycol Solvate

Propylene glycol (24 ml) was added to Darunavir (8 g) at 30-40° C. and stirred at 45-50° C. under reduced pressure for 20 minutes. The resulting solution was cooled to 25-30° C. and stirred at this temperature, for 5 h. The separated product was filtered, washed with propylene glycol (5 ml) and dried at 45-50° C. under reduced pressure to obtain Darunavir propylene glycol solvate.

Yield: 4.9 g

Example 12

Preparation of Darunavir Trimethylene Glycol Solvate

Trimethylene glycol (24 ml) was added to Darunavir (8 g) at 30-40° C. and stirred at 45-50° C. under reduced pressure for 20 minutes. The resulting solution was cooled to 25-30° C. and stirred at this temperature for 5 h. The separated product was filtered, washed with trimethylene glycol (5 ml) and dried at 45-50° C. under reduced pressure to obtain Darunavir trimethylene glycol solvate.

Yield: 4.8 g

Example 13

Preparation of Darunavir 2-Methoxyethanol Solvate

2-Methoxyethanol (24 ml) was added to Darunavir (8 g) at 30-40° C. and stirred at 45-50° C. under reduced pressure for 20 minutes. The resulting solution was cooled to 25-30° C. and stirred at this temperature for 5 h. The separated product was filtered, washed with 2-methoxyethanol (5 ml) and dried at 45-50° C. under reduced pressure to obtain Darunavir 2-methoxyethanol solvate.

Yield: 4.8 g

Example 14

Preparation of Amorphous Darunavir

Darunavir ethylene glycol solvate (3 g) was suspended in DM water (30 ml) at 25-30° C. and stirred at this temperature for 15 h. The slurry was filtered, washed with DM water (6 ml) and dried at 55-60° C. under reduced pressure to obtain amorphous Darunavir.

Yield: 1.7 g
Water content: 0.63%

Example 15

Preparation of Amorphous Darunavir

Darunavir propylene glycol solvate (2 g) was suspended in DM water (20 ml) at 25-30° C. and stirred at this temperature for 15 h. The slurry was filtered, washed with DM water (4 ml) and dried at 55-60° C. under reduced pressure to obtain amorphous Darunavir.

Yield: 1.6 g
Water content: 1.0%

Example 16

Preparation of Amorphous Darunavir

Darunavir trimethylene glycol solvate (2 g) was suspended in DM water (20 ml) at 25-30° C. and stirred at this temperature for 15 h. The slurry was filtered, washed with DM water (4 ml) and dried at 55-60° C. under reduced pressure to obtain amorphous Darunavir.

Yield: 1.2 g
Water content: 1.1%.

Example 17

Preparation of Amorphous Darunavir

Darunavir 2-methoxyethanol solvate (2 g) was suspended in DM water (20 ml) at 25-30° C. and stirred at this temperature for 15 h. The slurry was filtered, washed with DM water (4 ml) and dried at 55-60° C. under reduced pressure to obtain amorphous Darunavir.

Yield: 1.6 g
Water content: 0.69%

Example 18

Preparation of Amorphous Darunavir

Darunavir ethanolate (3 g) was suspended in DM water (30 ml) at 25-30° C. and stirred at this temperature for 15 h. The slurry was filtered, washed with DM water (6 ml) and dried at 55-60° C. under reduced pressure to produce amorphous Darunavir.

Yield: 2.4 g
Water content: 0.67%

Example 19

Preparation of Amorphous Darunavir

Darunavir (2 g) was stirred in a mixture of methanol (2 ml) and DM water (18 ml) at 25-30° C. for 15 h. The obtained solid was filtered, washed with D M water and dried at 55-60° C. under reduced pressure to obtain amorphous Darunavir.

Yield: 1.6 g
Water content: 0.26%

Example 20
Preparation of Tablet Dosage Form of Darunavir

| Ingredients | Qty (% w/w)/tablet |
|---|---|
| Darunavir (as propylene glycolate) | 5-60% |
| Microcrystalline cellulose | 10-80% |
| Colloidal silicon dioxide | 0.01-5% |
| Crospovidone | 1-20% |
| Magnesium stearate | 0.01-5% |

We claim:
1. Propylene glycol solvate of Darunavir.
2. A process for the preparation of propylene glycol solvate of Darunavir of claim 1, which comprises:
   a) treating Darunavir with propylene glycol, optionally in presence of a solvent; and
   b) isolating propylene glycol solvate of Darunavir.
3. The process according to claim 2, wherein the solvent comprises methyl tert-butylether and diisopropylether or mixtures thereof.
4. An improved process for the preparation of propylene glycol solvate of Darunavir of Formula I,

I which comprises,
a) reacting epoxide compound of Formula V,

V wherein, P represents a protecting group;
with isobutylamine in presence or absence of a solvent to give a compound of Formula VII;

VII wherein, P represents a protecting group;
b) optionally, isolating the compound of Formula VII;
c) reacting the compound of Formula VII with p-nitrobenzenesulfonyl halide or its acid addition salts to give a compound of Formula VIII or acid addition salt thereof;

VIII wherein, P represents a protecting group;
which is free of impurity compound of Formula XI;
d) deprotecting the compound of Formula VIII or acid addition salt thereof, to give a compound of Formula IX or acid addition salt thereof;

IX e) reducing the compound of formula IX or acid addition salt thereof to give Diamino alcohol of Formula II or acid addition salt thereof;

II f) condensing compound of Formula II with 1-[[[(3R,3aS,6aR)-hexahydrofuro[2,3-b]furan-3-yloxy]carbonyl]oxy]-2,5-pyrrolidine-dione of Formula X,

X in a solvent to give Darunavir of Formula I; and
g) converting the Darunavir of Formula I into its propylene glycol solvate.
5. The process according to claim 4, wherein the solvent in step (a) comprises of alcohols, ethers, hydrocarbons, halogenated hydrocarbons, N,N-dimethylformamide, N,N-dimethylacetamide, dimethylsulfoxide or mixtures thereof.

6. The process according to claim 4, wherein the solvent methanol, ethanol, isopropanol, tetrahydrofuran, dioxane, toluene, xylene, cyclohexane, hexane, ethylene chloride, ethylene chloride, chloroform or mixtures thereof.

7. The process according to claim 4, wherein the acid scavenger comprises non-nucleophilic inorganic or organic bases.

8. The process according to claim 4, wherein the reducing agent comprises borane complex, metal, transition metal in the presence of hydrogen or hydrogen source.

9. The process according to claim 4, wherein the solvent in step (f), comprises methylene chloride, chloroform, methanol, acetonitrile, tetrahydrofuran or mixtures thereof.

10. The process according to claim 4, wherein the acid addition salt comprises hydrochloride, hydrobromide, or sulfate.

11. A pharmaceutical composition comprising an effective amount of Darunavir propylene glycol solvate of Darunavir of claim 1 and at least one pharmaceutically acceptable excipient.

12. The pharmaceutical composition according to claim 11, wherein the composition is a solid dosage form.

13. A method of treating retroviral infections in a humans in need thereof which comprises administering to a human a therapeutically effective amount of propylene glycol solvate of Darunavir of claim 1.

* * * * *